Feb. 7, 1967 D. L. ARMSTRONG Plant Pat. 2,707
ROSE PLANT
Filed Nov. 17, 1965
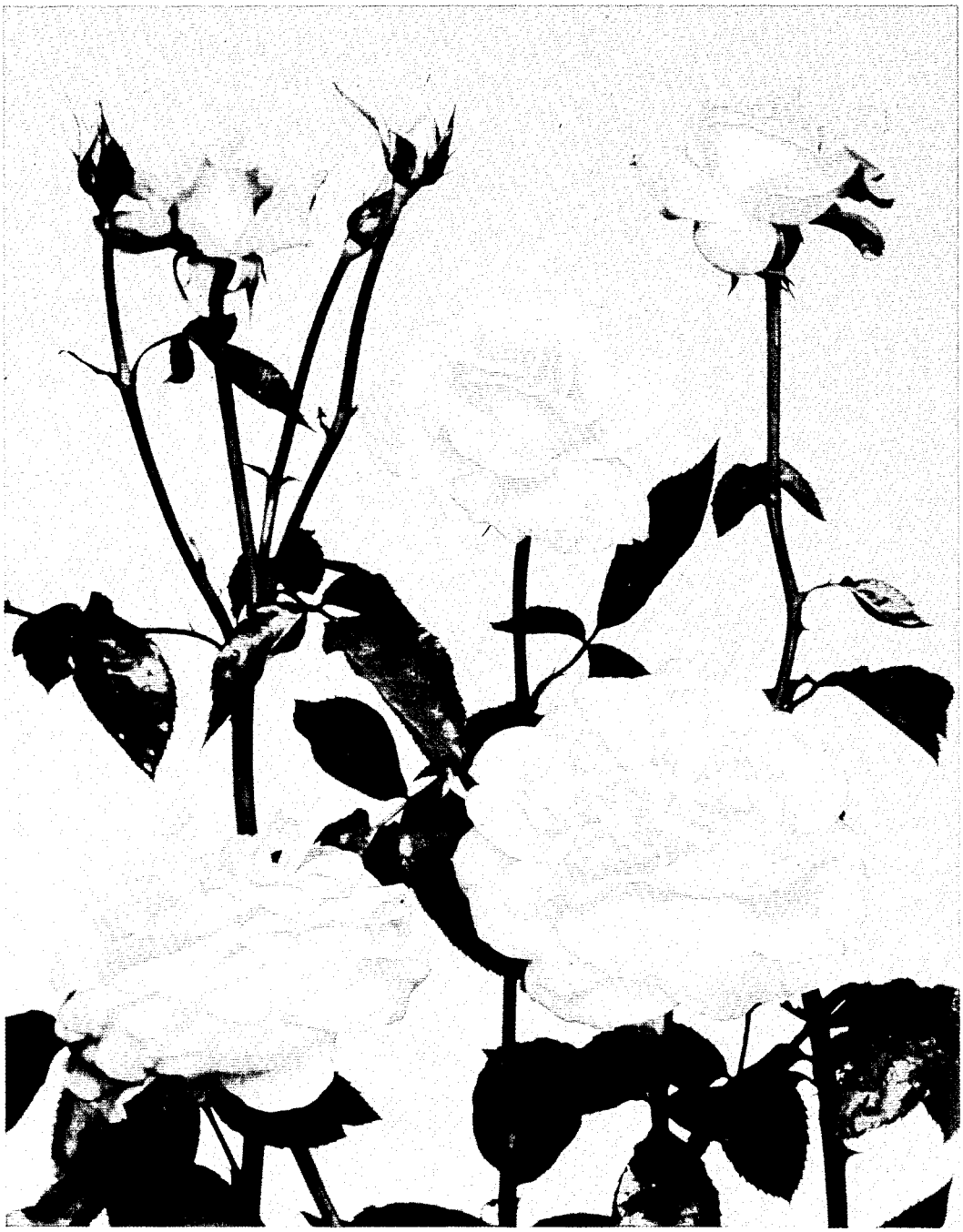
Inventor.
D. L. Armstrong
By: Robb & Robb
Attorneys.

United States Patent Office

Plant Pat. 2,707
Patented Feb. 7, 1967

2,707
ROSE PLANT

David L. Armstrong, Ontario, Calif., assignor to Armstrong Nurseries, Inc., Ontario, Calif., a corporation of California Filed Nov. 17, 1965, Ser. No. 508,400
1 Claim. (Cl. Plt.—25)

The present invention relates to a new and distinct variety of rose plant of a class falling intermediate the hybrid tea and floribunda classes, which was originated by me by crossing the variety known as "Ma Perkins" (Plant Patent No. 1,143) and the variety known as "Spartan" (Plant Patent No. 1,357), the former being the seed parent and the latter being the pollen parent.

The general objectives of this breeding was to produce a new and improved rose variety falling in a class intermediate the hybrid tea floribunda classes, while bearing flowers of a color ranging in the coral-pink, orange to orange-red colors. This objective was fully achieved, along with other desirable improvements, as evidenced by the following unique combination of characteristics which are outstanding in the new variety and which distinguish it from its parents, as well as from all other varieties of which I am aware:

(1) A vigorous upright, bushy and much-branched plant habit;

(2) A quite floriferous habit, with the flowers borne sometimes singly and sometimes from 2 to 5 to the stem;

(3) An excellent urn-shaped bud form;

(4) Double flowers of medium size; and (5) A distinctive and very attractive flower color ranging between Mandarin Red and Scarlet, but becoming lighter with age.

In comparison with its seed parent "Ma Perkins," the new variety differs primarily therefrom in having a more orange-red and darker color than the shell pink color which is typical of the flowers of this parent.

As compared with its pollen parent "Spartan," the new variety is more vigorous, has more perfect urn-shaped buds, with the flowers being of somewhat less petalage, while the flower color is somewhat lighter orange-red color.

Asexual reproduction of my new variety by budding, as performed at Ontario, California, shows that the foregoing characteristics and distinctions come true to form and are established and transmitted through succeeding propagations.

The accompanying drawing shows typical specimens of the vegatative growth and flowers of my new variety in different stages of development as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W) and Robert Ridgway's Color Standards and Nomenclature (hereinafter abbreviated (R)), as indicated:

Type: Tall; bush; outdoor; seedling; for cut flowers and for garden decoration.

Class: Intermediate hybrid tea and floribunda classes.

Breeding: Seedling.

*Seed parent.*—"Ma Perkins."

*Pollen parent.*—"Spartan."

Propagation: Holds its distinguishing characteristics through succeeding propagations by budding.

*Flower*

Locality where grown and observed: Ontario, California.

Flowers borne: Sometimes singly and sometimes from 2 to 5 to stem; in irregular clusters; on stems of medium length and normal strength.

Quantity of bloom: Abundant, outdoors.

Continuity: Nearly continuous during growing season.

Fragrance: From slight to moderate.

Bud:

*Peduncle.*—From short to average length; average caliper; erect; usually smooth; with several to many small stipitate glands. Color—near Courage Green, Plate XVII (R), overlaid with near Indian Red, Plate XXVII (R) on side exposed to sun.

*Before calxy breaks.*—Size—small. Form—short; pointed; between oviod and globular.

*As calyx breaks.*—Color—near Jasper Red, Plate 018, page 107 (W), overlaid with near Cardinal Red, Plate 822/1, page 168 (W) on area exposed to sun longer.

*Sepals.*—Inner surface—with fine, wooly tomentum. Outer surface—usually with many small stipitate glands. Alternate margins—lined with fine, wooly tomentum. Other margins—with many small stipitate glands and small slender foliaceous parts.

*As first petal opens.*—Size—small. Form—short; from oviod to usually urn-shaped. Color: Outside—between Scarlet, Plate 19/2, page 19 (W) and Geranium Lake, Plate 20/2, page 20 (W); inside—near Scarlet, Plate 19/1, page 19 (W), blending with near Vermilion, Plate 18, page 18 (W) toward base of petal, with small area at base of petal near Lemon Yellow, Plate 4, page 4 (W).

*Opening.*—Opens up well; is not retarded or prevented from opening by cold, hot, wet or dry weather.

Bloom:

*Size (when full open).*—Average; from 3 inches to 4 inches.

*Petalage.*—Double; from 20 to 35 petals; plus 10 to 15 petaloids; arranged irregularly.

*Form.*—High-centered at first, but becoming cupped to high-centered; petals being at first tightly cupped, with tips reflexed outward, but later becoming more loosely flat to cupped, with tips reflexed outward; outside petals of newly opened flower reflexed strongly outward along both apex and edges; intermediate petals of newly opened flower reflexed slightly outward along apex and edges; outside and intermediate petals of 3-days open flower reflexed strongly outward along both apex and edkes.

Petals:

*Texture.*—Medium thickness; moderately leathery.

*Apparance.*—Inside—from satiny to velvety. Outside—satiny.

*Shape.*—Outside—between round and broadly obovate, with apex flat and usually with 1 or 2 notches. Intermediate—broadly obovate, with apex rounded to flat and sometimes with 1 or 2 notches. Inside—broadly obovate, with apex rounded and sometimes with 1 or 2 notches.

This description of a newly opened flower was made from a rose grown outdoors during the month of September at Ontario, California:

*Color.*—Outer petal: Outside surface — between Scarlet, Plate 19/2, page 19 (W) and Geranium Lake, Plate 20/2, page 20 (W), with small area at base of petal near Sap Green, Plate 62/1, page 62 (W); inside surface—near Geranium Lake, Plate 20/1, page 20 (W), blending with near Scarlet, Plate 19/1, page 19 (W) toward base of petal, with small area at base of petal near Primrose Yellow, Plate 601, page 65 (W). Intermediate petal: Outside surface—between Vermilion, Plate 18/2, page 18 (W) and Scarlet, Plate 19/2, page 19 (W), with small area at base of petal near Dresden Yellow, Plate 64/1, page 64 (W); inside surface—near Vermilion, Plate 18/1, page 18 (W), blending with near Poppy Red, Plate 16, page (W), with small area at base of petal near Primrose Yellow, Plate 601, page 65 (W). Inner petal: Outside surface—between Mandarin Red, Plate 17/1, page 17 (W) and Vermilion, Plate 18/1, page 18 (W), with small area at base of petal near Dresden Yellow, Plate 64/1, page 64 (W); inside surface—between Poppy Red, Plate 16 page, 16 (W) and Mandarin Red, Plate 17, page 17 (W), with small area at base of petal near Empire Yellow, Plate 603, page 66(W).

This description was made from a rose that was open for three days outdoors during the month of September at Ontario, California:

*Color.*—Outer petal: Outside surface—between Geranium Lake, Plate 20/3, page 20 (W) and Carmine, Plate 21/3, page 21 (W), with small area at base of petal near Dresden Yellow, Plate 64/3, page 64 (W); inside surface—near Carmine Rose, Plate 621, page 75 (W), blending with Porcelain Rose, Plate 620, page 147 (W) toward base of petal, with small area at base of petal near Primrose Yellow, Plate 601/3, page 65 (W). Inner petal: Outside surface—near Camellia Rose, Plate 622/2, page 148 (W), with small area at base of petal near attachment near Primrose Yellow, Plate 601/3, page 65 (W); inside surface—between Porcelain Rose, Plate 620, page 147 (W) and Camellia Rose, Plate 622/1, page 148 (W), with small area at base of petal near Primrose Yellow, Plate 601/2, page 65 (W).

*General color effect.*—Newly opened flower—between Mandarin Red, Plate 17/1, page 17 (W) and Scarlet, Plate 19/2, page 19 (W). 3-days open—between Carmine Rose, Plate 621, page 75 (W) and Porcelain Rose, Plate 620/1, page 147 (W).

*Behavior.*—Drop off cleanly; not particularly affected by cold, hot, wet or dry weather.

*Flower longevity.*—On bush in garden—4 or 5 days in June. Cut roses grown outdoors and kept at livingroom temperatures—3 or 4 days in June.

*Reproductive organs*

Stamens: Average number; arranged regularly about pistils; a few mixed with petaloids.

Filaments: From short to medium length (from 4 mm. to 10 mm. long); most with anthers. Color—near Aureolin, Plate 3/2, page 3 (W).

Anthers: Small; all open approximately at once. Color: Upper side—margins near Saffron Yellow, Plate 7/1, page 7 (W), with remainder near Aureolin, Plate 3/2, page 3 (W); under side—same as upper side.

Pollen: Moderate quantity. Color — near Tangerine Orange, Plate 9/1, page 9 (W).

Pistils: From few to average number (approximately 50).

Styles: Uneven; from short to average length; thin; bunched. Color—upper ⅓ of style near Scarlet, Plate 19/2, page 19 (W), with remainder near Primrose Yellow, Plate 601/2, page 65 (W).

Stigma: Color—near Barium Yellow, Plate 503/2, page 131 (W).

Ovaries: Usually all enclosed in calyx.

Hips: Short; globular; smooth; walls thick and fleshy. Color (half mature)—near Kildare Green, Plate XXXI (R), overlaid with near Drab, Plate XLVI (R) on side exposed to sun.

Sepals: Falling soon; from short to medium length; straight. Color: Inside—near Smoke Gray, Plate XLVI (R); outside—near Rainette Green, Plate XXXI (R).

Seeds: From average number to many (6 to 15 per hip); from small to medium size.

*Plant*

Foliage:

*Leaves.*—Compound of usually 3–7 leaflets; normal abundance; from small to medium size; leathery; semi-glossy.

*Leaflet.* — Shape — oval. Apex — acute. Base — round. Margin—doubly serrated.

*Color.*—Mature: Upper surface—between Empire Green, Plate XXXII (R) and Dark Dull Yellow Green, Plate XXXII (R); under surface—near Light Elm Green, Plate XVII (R). Young: Upper surface—near Cress Green, Plate XXXI (R), overlaid with near Dark Mineral Red, Plate XXVII (R) along edges of leaflets; under surface—between Natal Brown, Plate XL (R) and Olive Brown, Plate XL (R).

*Rachis (the supporting stem of the compound leaf).*—From light to average size. Upper side—grooved; with many small stipitate glands on edges. Under side—smooth; with many small stipitate glands and few to several small prickles.

*Stipules.*—From short to medium length; narrow; with short points turning out at an angle of more than 45°.

*Disease resistance.*—Average resistance to mildew, as determined by comparison with other varieties grown under comparable cultural conditions at Ontario, California.

Growth:

*Habit.*—Bushy; upright; much-branched.

*Growth.*—Free.

*Canes.*—Medium caliper.

*Main stems.*—Color—near Light Cress Green Plate XXXI (R). Large prickles—several; from short to medium length; hooked slightly downward; with moderately narrow base of medium length; color—near Drab Gray, Plate XLVI (R). Small prickles—from several to many; color—near Drab Gray, Plate XLVI (R). Hairs—none.

*Branches.*—Color—near Biscay Green, Plate XVII (R). Large prickles—from several to many; medium length; hooked slightly downward; with moderately narrow base of medium length; color—near Cacao Brown, Plate XXVIII (R). Small prickles—few; color—near Cacao Brown, Plate XXVIII (R). Hairs—none.

*New shoots.*—Color—near Rainette Green, Plate XXXI (R), overlaid with near Sorghum Brown, Plate XXXIX (R) on side exposed to the sun. Large prickles—several; short; hooked slightly downward; with narrow base of medium length; color—near Mineral Red, Plate XXVII (R). Small prickles—few; color—near Mineral Red, Plate XXVII (R). Hairs—none.

I claim:

A new and distinct variety of rose plant of a class falling intermediate the hybrid tea and floribunda classes, substantially as herein shown and described, characterized particularly as to novelty by the unique combination of a vigorous, upright bushy and much-branched plant habit, a quite floriferous habit, with the flowers borne sometimes singly and sometimes from two to five to the stem, an excellent urn-shaped bud form, double flowers of medium size, and a distinctive and very attractive flower color ranging between Mandarin Red and Scarlet, but becoming lighter with age.

No references cited.

ABRAHAM G. STONE, *Primary Examiner.*

R. E. BAGWILL, *Examiner.*